(12) United States Patent
Shah (10) Patent No.: US 11,478,350 B2
(45) Date of Patent: Oct. 25, 2022

(54) AORTIC ANNULAR SUPPORT SYSTEM

(71) Applicant: University of Manitoba, Winnipeg (CA)

(72) Inventor: Pallav Shah, Winnipeg (CA)

(73) Assignee: University of Manitoba, Winnipeg (CA)

( * ) Notice: Subject to any disclaimer, the term of this patent is extended or adjusted under 35 U.S.C. 154(b) by 318 days.

(21) Appl. No.: 15/760,088

(22) PCT Filed: Sep. 16, 2016

(86) PCT No.: PCT/CA2016/051091
§ 371 (c)(1),
(2) Date: Mar. 14, 2018

(87) PCT Pub. No.: WO2017/045078
PCT Pub. Date: Mar. 23, 2017

(65) Prior Publication Data
US 2018/0263775 A1 Sep. 20, 2018

Related U.S. Application Data

(60) Provisional application No. 62/220,025, filed on Sep. 17, 2015.

(51) Int. Cl.
*A61F 2/24* (2006.01)
(52) U.S. Cl.
CPC .......... *A61F 2/2445* (2013.01); *A61F 2/2409* (2013.01); *A61F 2250/0004* (2013.01); *A61F 2250/0018* (2013.01)

(58) Field of Classification Search
CPC .................. A61F 2/24; A61F 2/2445
See application file for complete search history.

(56) References Cited

U.S. PATENT DOCUMENTS

| 5,607,471 A | 3/1997 | Seguin |
| 6,143,024 A | 11/2000 | Campbell et al. |

(Continued)

OTHER PUBLICATIONS

International Search Report and Written Opinion of the ISA/CA dated Nov. 22, 2016 in International Application No. PCT/CA2016/051091; 10pgs.

*Primary Examiner* — Matthew W Schall
(74) *Attorney, Agent, or Firm* — Michael R Williams; Ryan W Dupuis; Ade & Company Inc.

(57) ABSTRACT

A two-part aortic annular support system for supporting an aortic annulus during aortic valve repair procedures for prevention of further annular dilation. The first part comprises a composite annular ring that is positionable from within an aortic valve into the left ventricular outflow tract at the level of annular plane. The composite ring comprises a semi-rigid section and a resiliently deformable section. The semi-rigid section is shorter in length than the deformable section. The deformable section is extendible into a commissure of the aortic valve. The second part is a resilient band that is positionable external to the aortic root. The resilient band is securable to the composite ring through the aortic annulus by suturing. The present disclosure also relates to a use of the aortic annular support system and a method of inserting and securing the aortic annular support system during a surgical intervention.

10 Claims, 9 Drawing Sheets

(56) References Cited

U.S. PATENT DOCUMENTS

| | | |
|---|---|---|
| 7,922,763 B2 | 4/2011 | Song |
| 2005/0256569 A1 | 11/2005 | Lim et al. |
| 2009/0171457 A1* | 7/2009 | Song .................... A61F 2/2445 623/2.36 |
| 2011/0130830 A1 | 6/2011 | Lansac |
| 2013/0110231 A1* | 5/2013 | Dobrilovic ......... A61B 17/0483 623/2.41 |

* cited by examiner

AORTIC ANNULAR SUPPORT SYSTEM

RELATED APPLICATIONS

This application is a National Stage filing under 35 U.S.C. § 371 of International Application No. PCT/CA2016/051091 filed Sep. 16, 2016, which claims priority under 35 U.S.C. § 119(e) to U.S. Provisional Patent Application No. 62/220,025, filed Sep. 17, 2015, which applications are incorporated herein by reference.

TECHNICAL FIELD

The present disclosure relates to the field of medical devices that are implantable in the heart. In particular, the present disclosure relates to a medical device support system that is implantable during a surgical reconstruction, or repair, of an incompetent aortic valve.

BACKGROUND

The mammalian heart is an organ made up of four muscular chambers that function together to pump blood throughout the body. Each of the four chambers has an associated downstream one-way valve made up of movable, coapting leaflets which are also interchangeably referred to herein as cusps. The cusps coapt to prevent the backward flow of blood into their respective chambers, which is referred to as regurgitation. Two such heart valves, the aortic and pulmonary valves, also commonly known as the semi-lunar valves. The aortic valve is tricuspid and characterized by three cusps referred to as the right coronary cusp, the left coronary cusp and the non-coronary cusp. In 1-2% of the patient population, the aortic valve is bicuspid and comprises two cusps referred to as the conjoined cusp (fusion of right and left coronary cusp) and the non-conjoined (non-coronary) cusp. The aortic valve leaflets are attached within the aortic root to a triple-scalloped line of collagenous, fibrous tissue generally referred to as the aortic annulus, the basal ring or the ventriculoaortic junction. As such, a three-pointed crown-like structure serves to support the aortic valve leaflets. The U-shaped convex lower edges of each leaflet are attached to and suspended from the base of the aortic root, with the upper free edges of each leaflet free to move and project into the lumen of the aorta.

Two adjacent leaflets approach one another at one of the three points of said crown-like structure to define a commissure of the aortic valve. Behind each leaflet, the aortic vessel wall bulges outward forming a pouch-like dilatation known as the sinus of Valsalva. In the region located slightly above the level of the commissures, the aortic root merges with the tubular portion of the ascending aorta at a substantially planar transition zone commonly known as the sinotubular junction (STJ). The aortic root houses the aortic valve structure and generally includes a portion of the native aortic conduit that extends from the left ventricular outflow tract (LVOT) to the portion of ascending aorta (AA) slightly above the STJ.

The aortic valve is a critical component in maintaining adequate forward flow of oxygenated blood to the rest of the body. A number of diseases lead to dilation of the aortic root structure and aortic annulus, also called aneurysm or ectasia, which in turn negatively affect the ability of the aortic valve leaflets to coapt and close completely. This ensuing condition, known as aortic insufficiency, can severely diminish the heart's ability to effectively deliver blood to the rest of the body or to the heart muscle, and can lead to serious complications such as heart failure and/or death.

The aortic annulus may comprise about 55% of a fibrous portion and about 45% of a muscular portion. The fibrous portion is further divided into a fibrous part (about 40%) which lies below the non-coronary and the left coronary cusp and this is where the annulus dilates in different pathologies and about 15% is a membranous part which lies below non coronary cusp and right coronary cusp.

If aortic valve disease is diagnosed, the two primary treatment options are valve replacement or repair of the native valve. Aortic valve replacement options include implanting a mechanical valve, implanting a bioprosthetic valve, or the Ross Procedure.

Generally, valve repair is preferred over valve replacement due to the complications associated with replacement valves, including (i) limited durability for bioprosthetic replacement valves or (ii) the need for anticoagulation therapy in mechanical valves.

Valve repair may also provide the following advantages over valve replacement for at least the following reasons: (i) a lower operative risk; (ii) greater preservation of ventricular function; (iii) reduced thromboembolic risk; (iv) lowered anticoagulation requirements; (v) reduced risk for endocarditis; (vi) improved hemodynamic performance; (vii) improved long-term survival; and (viii) less costly.

Aortic valve preserving procedures are of two types: Primary Aortic Valve Repair and Valve Sparing procedures. (David Reimplantation technique and the Yacoub Remodelling technique). The typical Primary Aortic Valve Repair is performed in: Type 1a: ascending aortic dilation; Type 1c: annular dilation; Type 1d: cusp perforation; Type II: cusp prolapse; and Type III: cusp restriction. Type 2b: aortic root aneurysm is treated by Valve sparing procedures. All types of valve preserving require annular stabilization.

The most common Valve Sparing procedures are a David Reimplantation and a Yacoub Remodeling. During the David Reimplantation procedure, the aortic valve is preserved and securely sewn within a synthetic tube graft. During the Yacoub Remodeling procedure, all three aortic sinuses are replaced by means of a triple-tongue-shaped graft. Of these two techniques, the David Reimplantation technique has several advantages but is also technically more demanding.

A David Reimplantation involves the placement of a Dacron root prosthesis or synthetic aortic conduit over the scalloped native tissue, where it is sutured both below the valve leaflets through the valve annulus, and above the valve leaflets. The procedure is generally long and difficult to perform, and often results in leaflet concussion with the walls of the Dacron prosthesis during the ejection phase of the cardiac cycle. In addition, the absence of radial compliance of the Dacron root prosthesis does not allow a venturi effect of normal aortic sinuses which is an important for preserving valve dynamics and valve leaflet durability. As such, the normal valve physiology may be compromised in this valve-sparing intervention.

A Yacoub Remodelling involves scalloping the Dacron root prosthesis to essentially match the remaining native tissue, and using a running suture to attach the prosthesis to the native aortic root tissue. Although this method addresses some of the problems of the David Reimplantation technique, it does not directly constrain the aortic annulus, which has been shown to result in annular dilatation over time. As such, this procedure is not well suited for resizing a dilated annulus and may be limited to replacing aneurysmal aortic tissue.

Current practice is to use David Reimplantation in young patients who are diagnosed with marfans, bicuspid valves, dissections or annuloaortic ectasia. Yacoub remodeling is used typically used in older patients who are diagnosed with ascending aortic aneurysms, dilated sinuses and normal annulus.

Cusp pathology, such as cusp prolapse, may occur in isolation or in conjunction with aneurismal disease. Diagnosis of cusp prolapse can usually be made on preoperative echocardiography and is confirmed on surgical inspection. Surgical techniques that are available for the correction of cusp prolapse include free margin plication and free-margin resuspension. These techniques can be used alone or in combination and both provide stable mid-term results. Choice of technique may therefore be tailored to the cusp pathology encountered.

Annuloplasty techniques often make use of implantable supports, such as support rings, for stabilizing the aortic annulus. Without these supports, the pathology can lead to progressive annular dilation and recurrent aortic insufficiency.

There are many challenges with using typical support rings for aortic valve repairs. For example, the aortic annulus is oval or elliptical in shape. Experimental evidence suggests that internally positioned annular support rings are superior to externally placed annular support rings. This means, however, that the annular support ring is inserted below the aortic valve, which increases the risk of damaging the aortic valve during insertion. The aortic annulus is dynamic in nature and contracts in systole and relaxes in diastolic phase of the cardiac cycle. This dynamic functionality needs to be preserved during a repair procedure. The aortic annulus is not in a single plane, unlike the mitral valve and the tricuspid valve, but multiple planes because of external dissection limitations and internal attachment of aortic valve. Additionally, the aortic annulus is partly fibrous and partly muscular, which poses further surgical challenges. Furthermore, the aortic annulus is very close to a portion of the conduction tissue, damage to which should be avoided.

When using an internally placed annuloplasty ring, the sutures are exposed to greater tensile stresses as the dilated native tissue is urged to conform to the smaller annuloplasty ring solely by said sutures. Furthermore, the resizing load is transmitted through the sutures and the native tissue is exposed to larger and more focused pressures at the relatively small suture interface. This may lead to tissue trauma or suture tear-through.

SUMMARY

One exemplary embodiment of the present disclosure relates to an aortic annular support apparatus and system. The exemplary support system generally comprises (a) a composite annular ring and (b) a resilient band. The composite ring comprises a semi-rigid section and a resiliently deformable or flexible section. The semi-rigid section is shorter in length than the deformable section. The composite ring is positionable internally along the aortic annulus with the semi-rigid section positionable at the fibrous portion of annulus, and the resiliently deformable section is extendible into a commissure along the membranous and muscular portion of the aortic annulus. The resilient band is positionable outside the aortic root at the level of external dissection and is securable to the ring through the aortic annulus for providing additional support to the aortic annulus.

Some exemplary embodiments of the present disclosure relate to a method of supporting a repaired aortic valve with an aortic annular support apparatus disclosed herein. An exemplary method for installation of the aortic annular support apparatus during a cardiovascular procedure generally comprises the steps of:
 (i) positioning the composite ring within the aortic valve in the left ventricular outflow tract at the level of annular plane such that the semi-rigid section is placed horizontally along the fibrous annulus and the resiliently deformable section is placed along the perimeter of the aorta annulus along the membanous and muscular septum,
 (ii) positioning the resilient band outside of the aortic root opposite to at least one portion of the composite ring;
 (iii) inserting a suture first through the composite ring, then through the aortic annulus, then through the resilient band, and then tying off the suture adjacent to the resilient band thereby securing together the resilient band, the aortic annulus, and the composite ring, and
 (iv) repeating the suturing step (iii) at selected locations around the perimeter of the composite ring until the entire perimeters of the composite ring, aortic annulus, and resilient band are secured together.

The resiliently deformable section allows the composite ring to conform with and/or follow along a suture line that follows a perimeter of the aortic annulus along the membranous and muscular septum. The semi-rigid section of the composite ring is placed horizontally along the fibrous annulus. This two-section configuration of the ring may allow optimized annular reduction at the level of the fibrous portion of the aortic annulus in bicuspid and tricuspid valves while avoiding interference with conduction bundle tissue and dynamic motion of the annulus during the cardiac cycle. The resilient band provides strength and stability to the ring, which is important for long-term outcomes.

The exemplary aortic annular support apparatus and system disclosed herein may also preserve the dynamic motion or alternatively change in shape of the aortic annulus while restoring a competent functional aortic annulus.

BRIEF DESCRIPTION OF THE DRAWINGS

These and other features of the present disclosure will become more apparent in the following detailed description in which reference is made to the appended drawings.

DETAILED DESCRIPTION

The exemplary embodiments of the present disclosure relate to an aortic annular support apparatus and system for use during a surgical repair of aortic valve to treat and prevent further annular dilation while preserving the three-dimensional (3D) motion of the ventriculoaortic junction during the cardiac cycle.

The exemplary aortic annular support apparatus and support system is used to selectively remodel a dilated aortic annulus. The support system may adapt to the non-planar geometry of the aortic annulus during the systolic and diastolic phases of the cardiac cycle.

According to one exemplary embodiment, the aortic annular support apparatus and support system comprises a composite ring and a resilient band. The composite ring is generally planar and oval in shape, but is also deformable above and below plane. The use of this composite ring may allow surgeons to perform more durable valve-preserving surgical procedures by reducing and preventing further annular dilatation.

As used herein, the term "about" refers to an approximately +/−10% variation from a given value. It is to be understood that such a variation is always included in any given value provided herein, whether or not it is specifically referred to.

As used herein, the term "aortic valve" refers to a mammalian aortic valve, and it includes a tricuspid aortic valve and a bicuspid aortic valve.

As used herein, the terms "rigid" and "semi-rigid" refer a material or material property that is resistant to deforming and/or flexing under the pressure and flow conditions that would be expected when the exemplary support system of the present disclosure is inserted, as described further below, within a mammalian heart.

As used herein, the terms "deformable" and "flexible" refer a material or material property that deforms or flexes under the pressure and flow conditions that would be expected when the exemplary support system of the present disclosure is inserted, as described further below, within a mammalian heart.

The present disclosure will now be described by reference to FIGS. 1 to 9, which depict of examples of the aortic valve support system according to the present disclosure.

The present disclosure relates to an aortic annular support system 10 that comprises a ring 10A and a band 10B. The support system 10 is designed to be positioned about a bicuspid aortic valve 100 (shown in FIG. 2) and a tricuspid aortic valve 200 (shown in FIG. 6). In one example of the support system 10, the ring 10A may be positioned internally within the aortic valve 100, 200 (see FIGS. 5 and 9) and the band 10B may be positioned adjacent to and external to the aortic valve 100, 200.

Figure 1:
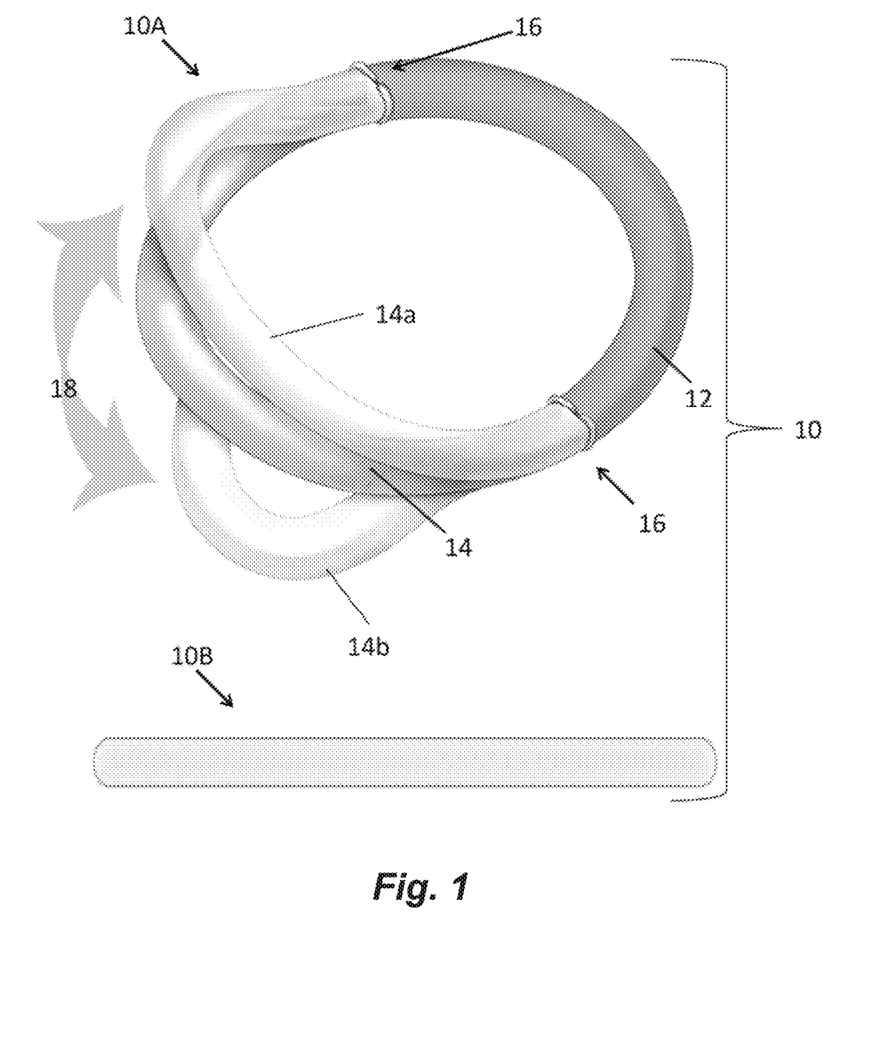
FIG. 1 is an isometric view of a composite annular ring and a resilient band according to one embodiment of the present disclosure for use in an aortic valve support system of the present disclosure.
Figure 2:
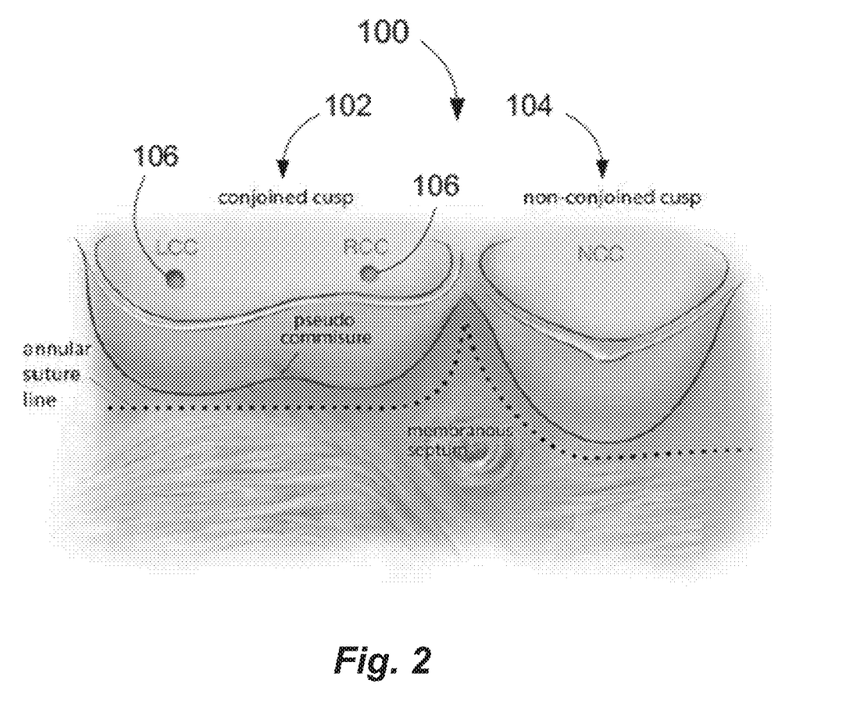
FIG. 2 is a schematic diagram of a laid open bicuspid aortic valve with a conjoined cusp and a non-conjoined cusp.

Referring to FIG. 1, the annular ring 10A comprises a first section 12 conjoined to a second section 14. The first section 12 may be rigid or semi-rigid and the second section 14 may be resiliently deformable/flexible. According to one exemplary embodiment, the first section 12 may occupy a single plane and the second section 14 may occupy the same single plane and may resiliently flex above (14a) and below that plane (14b) (see arrow 18 in FIG. 1). The ring 10A is a composite structure with each of the first and second sections 12, 14 forming a first section and a second section respectively, of the composite structure. According to one embodiment, the ends of the first section 12 may be tapered and extend into receptacles provided therefor in the ends of the second section 14. Alternatively, the ends of the first section 12 may each comprise a narrower diameter than the diameter of the annular ring between the two end sections, wherein the end sections with the narrower diameters extend into receptacles provided therefor in the ends of the second section 14. The overlapping junctures formed by the tapered ends of the first section 12, or alternatively the narrower diameter end sections extending in to the receptacles of the second section 14, may be secured by one or more connection members 16, such as a staple, a clip or a deformable connector. It is optional to encase the annular ring 10A in a resilient covering, which may also be referred to as a sheath.

The first section 12 may be of a given length and the second section 14 may be longer than the first section 12. For example, the first section 12 may be about the same length as a fibrous portion of the aortic annulus, which can be about 40% of the perimeter length of the aortic annulus. The second section may have a length that is about the same length as a non-fibrous portion of the aortic annulus, which can be about 60% of the perimeter length of the aortic annulus. According to one aspect of the ring 10A, the second section 14 may have a length that is between about 60% to about 75% of the perimeter length of the aortic annulus. In another aspect of the ring 10A, the second section 14 has a length that is about 65% of the perimeter length of the aortic annulus. The first and second sections 12, 14 may be curvilinear to form a generally elliptical, or oval shape, when viewed from above.

Figure 3:
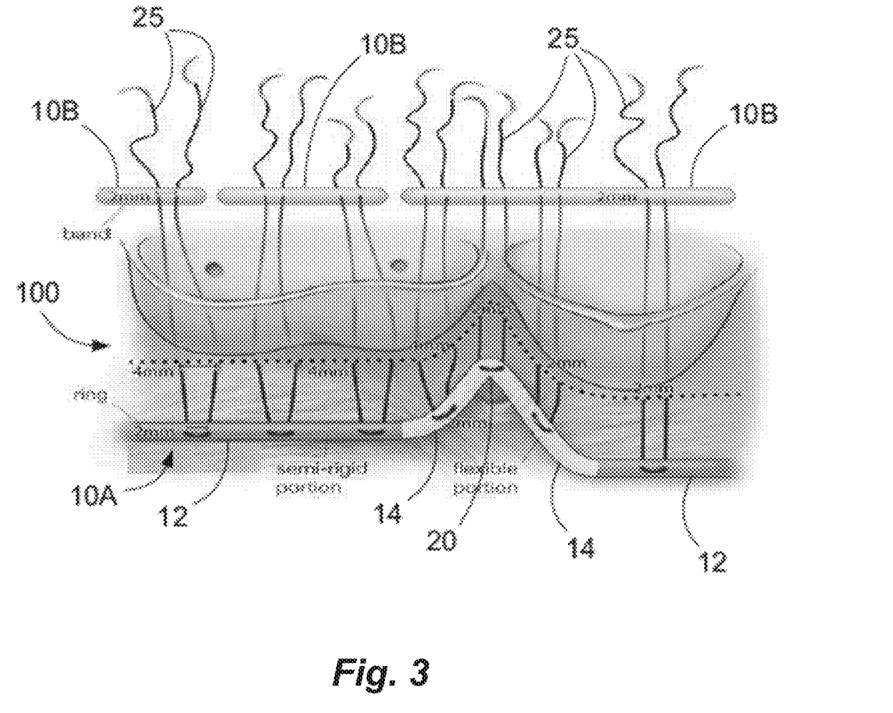
FIG. 3 is the schematic diagram of FIG. 2 with a composite annular ring and a resilient band of the present disclosure positioned about the bicuspid aortic valve with sutures in place for securing the ring and band to the bicuspid aortic valve.
Figure 4:
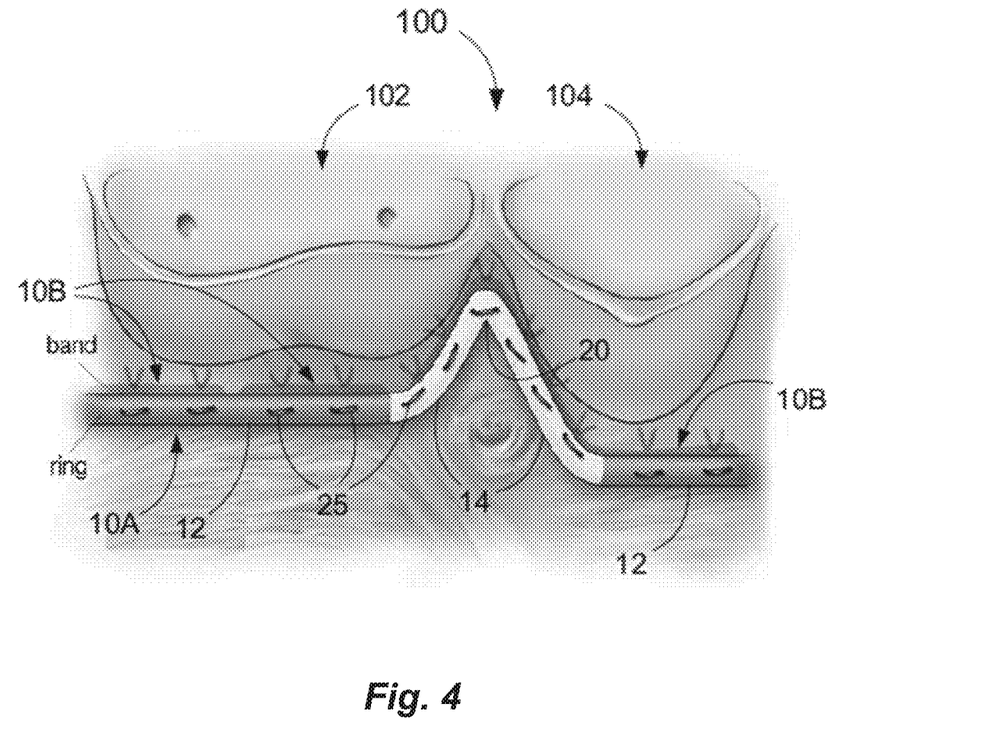
FIG. 4 is the schematic diagram of FIG. 3 with the sutures tightened and tied off.
Figure 5:
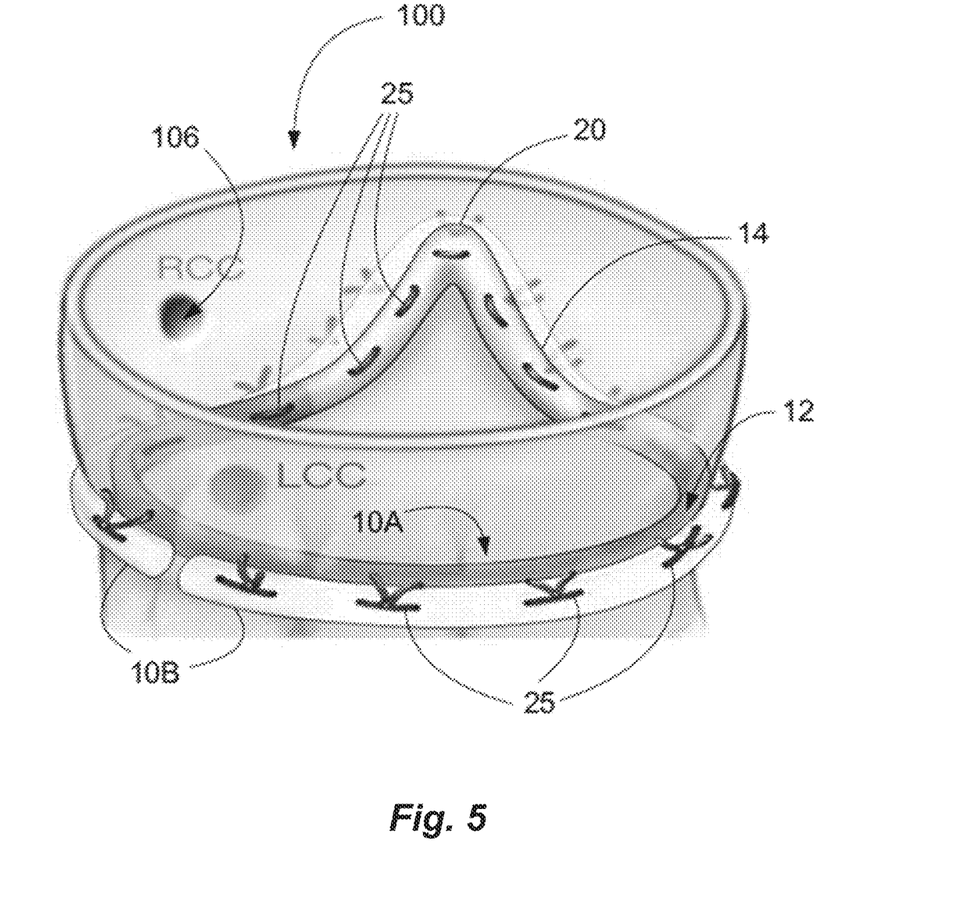
FIG. 5 is schematic diagram that depicts the arrangement of FIG. 4 from a non-laid open perspective.
Figure 6:
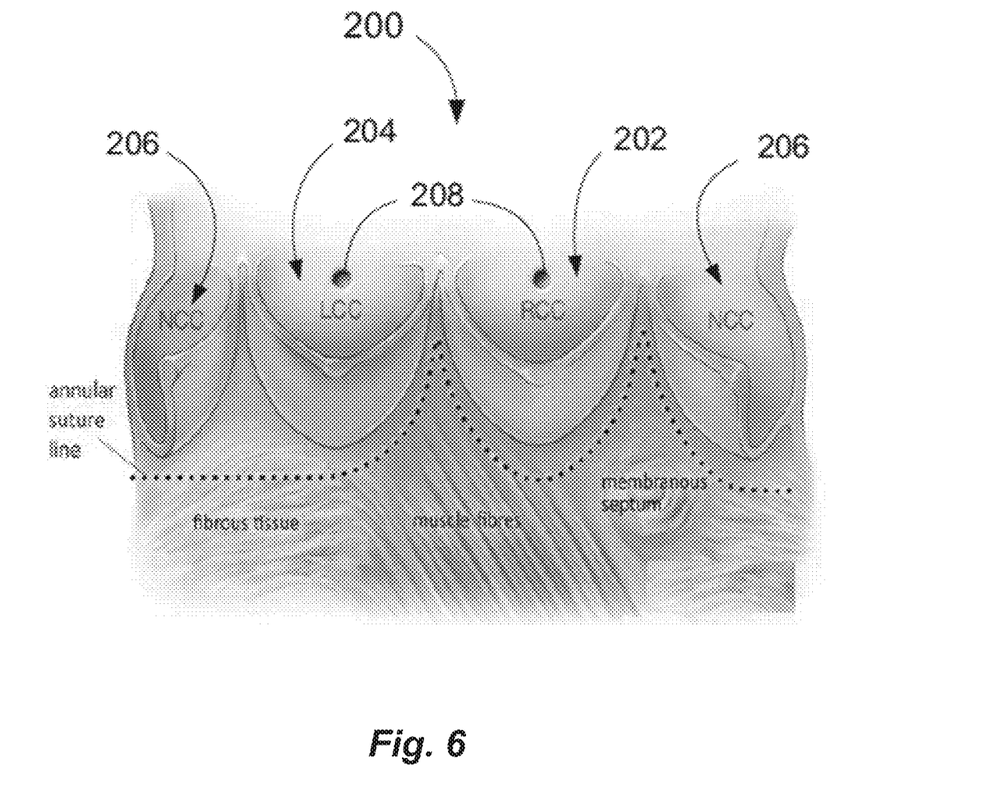
FIG. 6 is a schematic diagram of a laid open tricuspid aortic valve with a right coronary cusp, a left coronary cusp and a non-coronary cusp.
Figure 7:
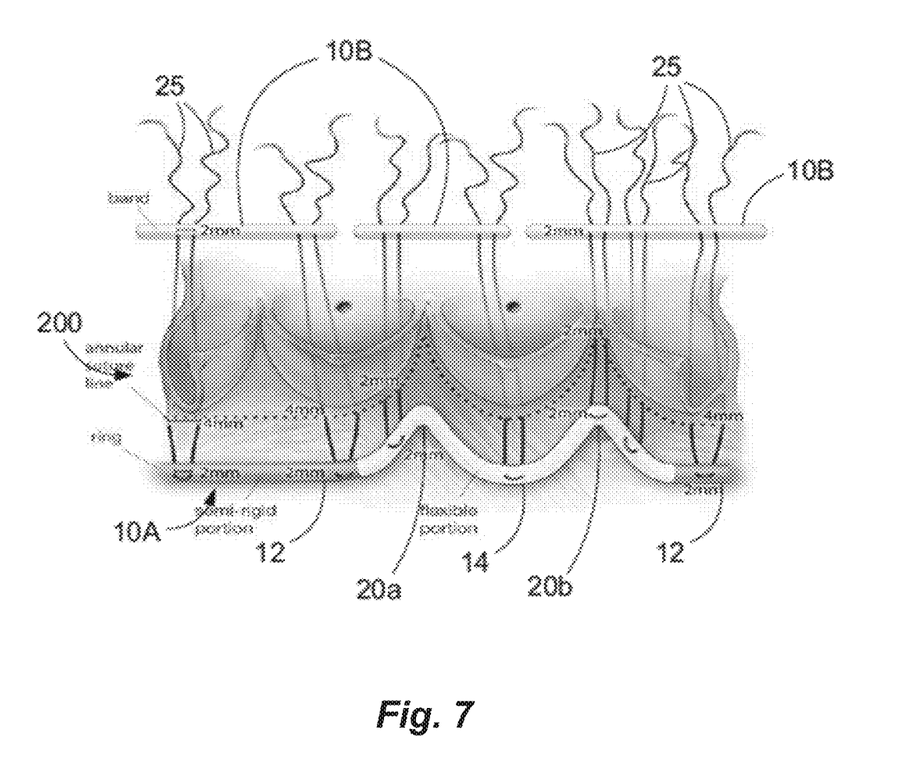
FIG. 7 is the schematic diagram of FIG. 6 with a composite annular ring and a resilient band of the present disclosure positioned about the tricuspid aortic valve with sutures in place for securing the ring and band to the tricuspid aortic valve.
Figure 8:
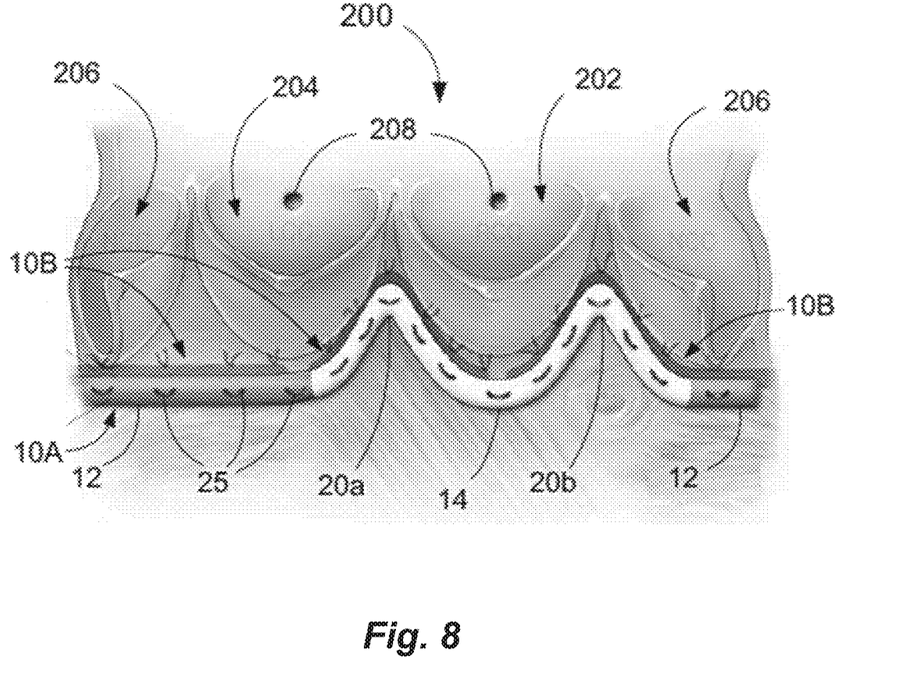
FIG. 8 is the schematic diagram of FIG. 7 with the sutures tightened and tied off.
Figure 9:
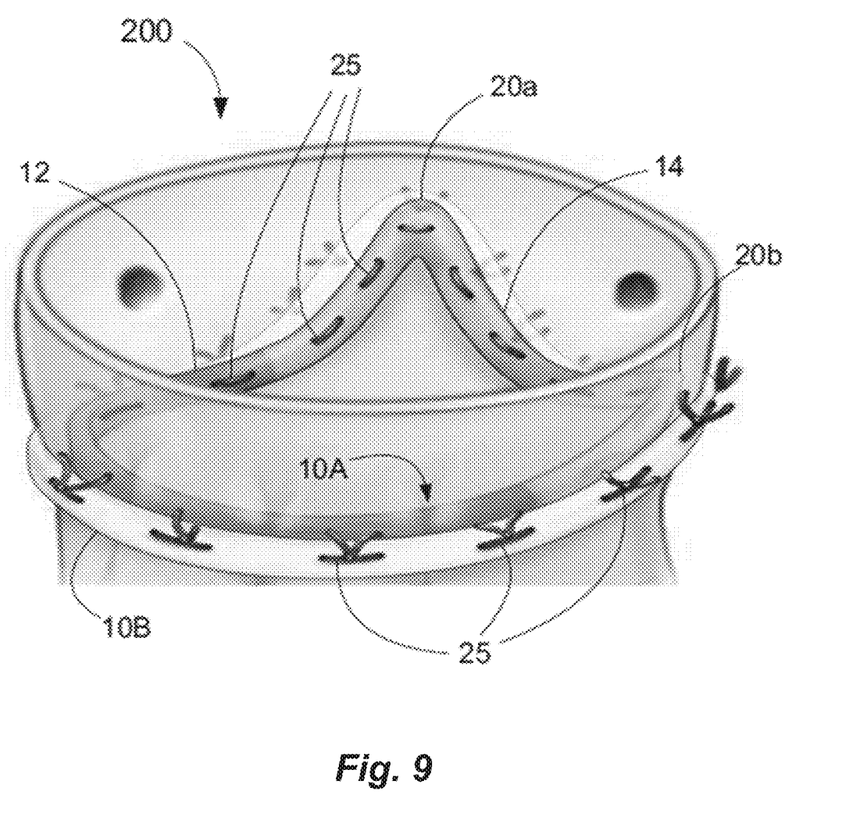
FIG. 9 is schematic diagram that depicts the arrangement of FIG. 8 from a non-laid open perspective.

According to another aspect of the ring 10A, the second section 14 may be deformed to define one or more extensions 20. FIGS. 4 and 5 illustrate an exemplary embodiment of the ring 10A wherein the second section 14 defines an extension 20. FIGS. 7, 8 and 9 depict another example of the ring 10A where the second section 14 comprises two extensions 20A, 20B. As will be described further below, the one or more extensions 20 are securable within commissures of the aortic valve 100. For example, the second section 14 may be deformed to define one extension 20 for extending between a conjoined cusp 102 and a non-conjoined cusp 104 of a bicuspid aortic valve 100 (as shown in FIGS. 3 to 5).

In another exemplary embodiment, the second section 14 of ring 10A may be deformed to define two extensions 20A and 20B. One extension 20A extends between the right coronary cusp 202 and the left coronary cusp 204. The other extension 20B extends between the right coronary cusp 202 and the non-coronary cusp 206 (see FIGS. 7 to 9).

The band 10B may be secured external to the aortic root by connecting the band 10B to the ring 10A for reinforcing the ring 10A. For example, the band 10B may define one or more gaps 10B' (i.e., a discontinuous perimeter) that accommodate for one or more of the coronary arteries that originate from the coronary ostia 106, 208, which are located in the right and left aortic sinuses (for example, as shown in FIGS. 3 and 5).

According to another exemplary embodiment of the present support system 10, the ring 10A has a cross-sectional width of about 3 mm to 5 mm and a cross-sectional height of about 5 mm to 7 mm. The first section 12 may be made of a material exemplified by any one of MP35N, cobalt-chromium, titanium-MC3, nitinol cell structure, or the like.

The second section 14 may be made of a silicone rubber strip that is covered by a material exemplified by polyester velour fabric, by polytetrafluoroethylene (PTFE), by DACRON° (DACRON is a registered trademark of Invista North America S.A.R.L. Corp, Wilmington, Del., USA), or a polyester fabric, and the like. The ring 10A may optionally further include a handle and a holder to facilitate insertion into the aortic valve 100, 200. The ring 10A may optionally include a sizer. Table 1 below provides a variety of suitable dimensions for the annular ring 10A for installation into an adult patient. The diameter of the sinotubular junction can be determined intraoperatively by different methods and formulas adopted by surgeons per their individual choices.

The diameter of the composite annular ring 10A for installation into an adult patient may be from the range of about 22 mm to about 36 mm. It is preferred that the ratio of the perimeter length of the first semi-rigid/rigid section to the perimeter length of the second resiliently deformable section is from the range of about 1:1.4 to about 1:1.8. It is suitable for the perimeter length of the resiliently deformable section to be about 5% greater in length than the perimeter length of the semi-rigid/rigid section.

The resilient band 10B may have a cross-sectional width between about 3 mm to 5 mm and cross-sectional height of 5 mm to 7 mm. The resilient band 10B may be made of a PTFE and polyester fabric. The diameter of the resilient band 10B is preferably about the same as the diameter of the composite annular ring 10A with which it is matched.

second section of the 14 of the ring 10A is substantially aligned with a curved section of the suture line which in turn, is substantially aligned with the muscular and membranous portion of the aortic annulus. The curved section of the suture line will extend into the commissures. For example, on a bicuspid aortic valve 100, the curved section of the suture line will extend between the conjoined cusp and the non-conjoined cusp (see FIG. 2). On a tricuspid aortic valve 200, the curved section of the suture line will extend into the commissures between the right coronary cusp and the non-coronary cusp—this region is also referred to as the membranous septum—and between the right coronary cusp and the left coronary cusp, which is also referred to as the muscular septum (see FIG. 6).

As depicted in FIGS. 3 and 7, sutures 25 are first inserted through the composite ring 10A, then through the suture line at the level of annulus and then through the resilient band 10B so that a suture loop is formed on the ring 10A. Through the first section 12 of the ring 10A, a given suture may be separated from itself by about 2 mm. Through the straight section of the suture line (i.e. through the fibrous portion of the aortic annulus), a given suture may be separated from itself between about 2 mm and about 4 mm for annular reduction. Through the corresponding section of the band 10B, the sutures may be about 2 mm apart.

The sutures may be inserted through any part of the second section 14 of the ring 10A and any part of the band 10B that is adjacent the straight portion of the suture line

TABLE 1

| STJ/Annular (D, mm) | Circumference(cm) 2 mm | Semirigid 40% (mm) | Flexible 60% (mm) | Flexible Extra: mm | Flexible mm | Ring size SR + F-mm |
|---|---|---|---|---|---|---|
| 24 | 7.54 | 3.01 | 4.53 | 0.70 | 5.23 | 8.24 |
| 26 | 8.17 | 3.30 | 4.87 | 0.70 | 5.57 | 8.87 |
| 28 | 8.80 | 3.50 | 5.30 | 0.70 | 6.00 | 9.50 |
| 30 | 9.43 | 3.80 | 5.63 | 0.70 | 6.33 | 10.13 |
| 32 | 10.06 | 4.00 | 6.06 | 1.00 | 7.06 | 11.06 |
| 34 | 10.69 | 4.30 | 6.39 | 1.00 | 7.39 | 11.69 |
| 36 | 12.39 | 4.96 | 7.43 | 1.00 | 8.43 | 13.39 |

Another exemplary embodiment of the present disclosure relates to a method of inserting the support system 10. Suitable sutures for this method may be 2.0 TICRON® or ETHIBOND® (ETHIBOND is a registered trademark of the Johnson and Johnson Corporation, New Brunswick, N.J., USA) with small needles attached at each end of the suture. Alternatively, other surgically relevant connections may be used that can secure the support structure 10 as described below. Optionally, the ring may have 2-mm markings for guiding the placement of the sutures and may comprise different colors or shading to mark the transition zones between the first and second sections 12, 14.

The exemplary support system 10 may be inserted into a patient after the surgical area proximal the aortic valve 100, 200 (FIGS. 2, 6) has been dissected externally and before the repair procedure begins. The ring 10A may be inserted using a holder and/or a handle. At a distance of at least 1 mm to 2 mm below the aortic valve cusps, the ring 10A is positioned and the band 10B is positioned opposite to the ring 10A, at the level of external dissection. The suture line substantially follows the perimeter of the aortic annulus and the suture line is positioned between the ring 10A and the band 10B.

The first section 12 of the ring 10A is aligned with a straight section of the suture line, which is substantially aligned with the fibrous portion of the aortic annulus. The (i.e. through the fibrous portion of the aortic annulus) with the same separation distances described above. For any part of the second section 14 of the ring 10A that is adjacent the curved portion of the suture line (i.e. through the muscular and membranous portion of the aortic annulus) the sutures may be inserted through all three structures with a spacing of about 2 mm.

After the sutures have been inserted through the support system 10 and the suture line, using the suture spacing described above, the sutures can then be tightened.

Next, the sutures along the first section 12 of the ring 10A may be tied off adjacent the band 10B, followed by tying off the sutures at the nadir, of the conjoined cusp 102 or the right coronary cusp 202, as the case may be. The holder can then be removed from the ring 10A and the remaining sutures can be tied off (see FIGS. 4 and 8).

FIG. 5 depicts the support system 10 in use securing and supporting a bicupid aortic valve 100. FIG. 9 depicts the support system 10 in use securing and supporting a tricuspid aortic valve 200.

An alternative way of inserting and fixing ring at the annulus is to dissect the root outside the non-coronary sinus in both directions towards the coronary ostia. In this area, the semi-rigid portion of the ring can be fixed by taking sutures from inside to outside the root as described earlier. The flexible portion of the ring can be fixed by stitches taken from inside the outflow tract into the sinus of the left and right coronary leaflets.

The invention claimed is:

1. A two-part aortic annular support apparatus comprising:
- a composite annular ring comprising a semi-rigid section conjoined to a resiliently deformable section, said annular ring positionable within an aortic valve into a left ventricular outflow tract at the aortic annular plane, wherein the semi-rigid section is configured for alignment with a fibrous portion of the aortic annulus and the resiliently deformable section is configured for alignment with a muscular and membranous portion of the aortic annulus and is extendible into a commissure of the aortic valve; and
- a discontinuous resilient band defining at least one gap, said discontinuous resilient band positionable external to an aortic root wherein said annular ring has been positioned, said band securable through the aortic annulus to the annular ring whereby said at least one gap accommodates therethrough at least one coronary artery.

2. The aortic annular support apparatus of claim 1, wherein a diameter of the composite annular ring to is selected from a range of about 22 mm to about 36 mm.

3. The aortic annular support apparatus of claim 2, wherein a ratio of a perimeter length of the semi-rigid section of the annular ring to a perimeter length of the resiliently deformable section is selected from a range of 1:1.4 to 1:1.8.

4. The aortic annular support apparatus of claim 1, wherein the ends of the semirigid section of the annular ring are configured for insertion into receptacles provided therefor in the ends of the resiliently deformable section.

5. The aortic annular support apparatus of claim 1, wherein junctures of the semirigid section and the resiliently deformable section of the annular ring, are secured by connection devices.

6. The aortic annular support apparatus of claim 5 wherein the connection devices are selected from a group consisting of staples, clips, and deformable connectors.

7. The aortic annular support apparatus of claim 1, wherein the composite annular ring is encased with a resiliently pliable material.

8. Use of the aortic annular support apparatus of claim 1 for supporting an aortic valve following a repair procedure, wherein (i) said annular ring is positioned within an aortic valve into a left ventricular outflow tract at the aortic annular plane with the deformable section extending into a commissure of the aortic valve, (ii) said resilient band is positioned external to an aortic root wherein said annular ring has been positioned, and (iii) said resilient band is secured through the aortic annulus to the annular ring.

9. A method of supporting a repaired aortic valve with the two-part aortic annular support apparatus of claim 1, the method comprising steps of:
   (i) positioning the composite ring within the aortic valve in the left ventricular outflow tract at the level of annular plane such that the semi-rigid section is placed horizontally along the fibrous annulus and the resiliently deformable section is placed along the membranous and muscular septum;
   (ii) positioning the resilient band outside of the aortic root opposite to at least one portion of the ring such that at least one coronary artery is accommodated therethrough the at least one gap in the resilient band;
   (iii) inserting a suture first through the composite ring, then through the aortic annulus, then through the resilient band, and then tying off the suture adjacent to the resilient band thereby securing together the resilient band, the aortic annulus, and the composite ring; and
   (iv) repeating the suturing step (iii) at selected locations around the perimeter of the composite ring until the entire perimeters of the composite ring and aortic annulus are secured to the resilient band.

10. The aortic annular support apparatus of claim 1, wherein the at least one gap is a discontinuous perimeter.

\* \* \* \* \*